(12) United States Patent
Kil et al.

(10) Patent No.: US 7,820,640 B2
(45) Date of Patent: *Oct. 26, 2010

(54) METHODS FOR TREATING HEARING LOSS

(75) Inventors: Jonathan Kil, Seattle, WA (US); Eric D. Lynch, Lake Forest Park, WA (US)

(73) Assignee: Sound Pharmaceuticals Incorporated, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/862,030

(22) Filed: Jun. 4, 2004

(65) Prior Publication Data

US 2004/0220145 A1    Nov. 4, 2004

Related U.S. Application Data

(63) Continuation of application No. 10/337,251, filed on Jan. 3, 2003, now Pat. No. 6,815,434.

(60) Provisional application No. 60/345,813, filed on Jan. 4, 2002.

(51) Int. Cl.
*A61K 31/724*    (2006.01)
*A61K 31/519*    (2006.01)

(52) U.S. Cl. ............ 514/58; 514/262.1; 514/359; 514/365; 514/562; 514/706; 536/46

(58) Field of Classification Search ............ 514/58, 514/262.1, 365, 562, 706, 56, 359; 536/46
See application file for complete search history.

(56) References Cited

U.S. PATENT DOCUMENTS

| | | | |
|---|---|---|---|
| 4,352,799 A | 10/1982 | Renson | |
| 4,774,252 A | 9/1988 | Welter | |
| 5,385,726 A | 1/1995 | Baldew | |
| 5,795,909 A | 8/1998 | Shashoua | |
| 6,093,743 A | 7/2000 | Lai | |
| 6,177,434 B1 | 1/2001 | Kopke et al. | |
| 6,601,580 B1 | 8/2003 | Bloch | |
| 6,815,434 B2 | 11/2004 | Kil | |
| 2003/0157191 A1 | 8/2003 | Kil | |
| 2004/0220145 A1 | 11/2004 | Kil | |
| 2005/0147978 A1 | 7/2005 | Remacle | |
| 2006/0089313 A1 | 4/2006 | Kil | |

FOREIGN PATENT DOCUMENTS

| | | |
|---|---|---|
| DE | 3638124 A1 | 5/1988 |
| DE | 198 56 210 A1 | 4/2000 |
| EP | 1 609 479 A1 | 12/2005 |
| WO | 92/02221 A1 | 2/1992 |
| WO | 01/80832 A2 | 11/2001 |
| WO | 03045334 A2 | 6/2003 |
| WO | 2004/080486 A1 | 9/2004 |

OTHER PUBLICATIONS

Attanasio et al. (Acta otorhinolaryngologica Italica: organo ufficiale della Societa italiana di otorinolaringologia e chirurgia cervico-facciale, (Feb. 1999) 19 (1), pp. 6-11 (Abstract Sent).*
Kopke et al. (Hearing Research (2000), 149 (1-2), 138-146) (Abstract Sent).*
Herrick et al. (Clinical and Experimental Rheumatology, (May-Jun. 2000) 18 (3) 349-56).(Abstract Sent).*
Dawson et al. (Neuroscience Letters (Feb. 6, 1995) vol. 185, No. 1, pp. 65-69) (Abstract Sent).*
Palmer et al. (Pediatric Research (Apr. 1990) vol. 27, No. 4 pt 1, pp. 332-336) (Abstract Sent).*
Cuzzocrea et al. (British Journal of Pharmacology, (Jul. 2000) vol. 130, No. 6, pp. 1219-1226) (Absract Sent).*
Sies (Free Radical Biology & Medicine (1993), 14(3), 313-23)(Abstract Sent).*
Cotgreave, I.A., and P. Moldéus, "Lung Protection by Thiol-Containing Antioxidants," *Bull. Eur. Physiopathol. Respir.* 23:275-277, 1987.
Cotgreave, I.A., et al., "The Anti-Inflammatory Activity of Ebselen But Not Thiols in Experimental Alveolitis and Bronchiolitis," *Agents and Actions* 24(3-4):313-319, 1988.

(Continued)

*Primary Examiner*—Shaojia Anna Jiang
*Assistant Examiner*—Michael C Henry
(74) *Attorney, Agent, or Firm*—Christensen O'Connor Johnson Kindness PLLC

(57) ABSTRACT

In one aspect, the present invention provides otoprotectant compositions useful for ameliorating hearing loss. In some embodiments, the otoprotective compositions comprise at least one glutathione peroxidase mimic. In some embodiments, the otoprotective compositions comprise at least one glutathione peroxidase mimic and at least one otoprotectant selected from the group consisting of a xanthine oxidase inhibitor and a glutathione or glutathione precursor. In some embodiments, the otoprotective compositions comprise at least one glutathione peroxidase mimic, at least one xanthine oxidase inhibitor, at least one glutathione or glutathione precursor. In another aspect, the present invention provides methods for ameliorating hearing loss by administering to a subject an amount of an otoprotective composition that is effective to ameliorate hearing loss.

6 Claims, 5 Drawing Sheets

OTHER PUBLICATIONS

Dehne, N., et al., "In Vitro Effects of Hydrogen Peroxide on the Cochlear Neurosensory Epithelium of the Guinea Pig," *Hearing Research* 143(1-2):162-170, 2000 (abstract only).

Ferrer, J.V., et al., "Allopurinol and N-Acetylcysteine Avoid 60% of Intestinal Necrosis in an Ischemia-Reperfusion Experimental Model," *Transplantation Proceedings* 30:2672, 1988.

Gustafson, D.L., and C.A. Pritsos, "Inhibition of Mitomycin C's Aerobic Toxicity by the Seleno-Organic Antioxidant PZ-51,"*Cancer Chemother. Pharmacol.* 28:228-230, 1991.

McFadden, S.L., et al., "M40403, a Superoxide Dismutase Mimetic, Protects Cochlear Hair Cells From Gentamicin, But Not Cisplatin Toxicity," *Toxicology and Applied Pharmacology* 186:46-54, 2003.

Pritsos, C.A, et al., "PZ-51 (Ebselen) In Vivo Protection Against Adriamycin-Induced Mouse Cardiac and Hepatic Lipid Peroxidation and Toxicity," *Biochemical Pharmacology* 44(4):839-841, 1992.

Ren, X., et al., "A Novel Glutathione Peroxidase Mimic With Antioxidant Activity," *Archives of Biochemistry and Biophysics*, 387(2):250-256, 2001.

Rybak, L.P., and S. Somani, "Ototoxicity: Amelioration by Protective Agents," *Annals of the New York Academy of Sciences* 884:143-151, 1999 (abstract only).

Rybak, L.P., et al., "Effect of Protective Agents Against Cisplatin Ototoxicity," *The American Journal of Otology* 21(4):513-520, 2000.

Seidman, M.D., et al., "The Protective Effects of Allopurinol and Superoxide Dismutase-Polyethylene Glycol on Ischemic and Reperfusion-Induced Cochlear Damage," *Otolaryngology—Head and Neck Surgery*, 105(3):457-463, Sep. 1991.

Song, B.-B., and J. Schacht, "Variable Efficacy of Radical Scavengers and Iron Chelators to Attenuate Gentamicin Ototoxicity in Guinea Pig In Vivo," *Hearing Research* 94(1-2):87-93, 1996 (abstract only).

Usui, M., et al., "Pathogenic Role of Oxidative Stress in Vascular Angiotensin-Converting Enzyme Activation in Long-Term Blockade of Nitric Oxide Synthesis in Rats," *Hypertension* 34(4):546-551, 1999.

Vermeulen, N.P.E., et al., "Toxicity of Fotemustine in Rat Hepatocytes and Mechanism-Based Protection Against It," *Chemico-Biological Interactions* 110:139-158, 1998.

Lopez-Gonzalez, M.A., et al., "Ototoxicity Caused by Cisplatin Is Ameliorated by Melatonin and Other Antioxidants," *Journal of Pineal Research* 28:73-80, 2000.

Physicians Desk Reference, 51st ed., 1997, pp. 1194-1196.

"Cancer Multidrug Resistance," *Nature Biotechnology* 18(Supplement):IT18-IT20, 2000, reprinted from *Nature Biotechnology* 17:94-95, 1999.

Baldew, G.S., et al., "The Influence of Ebselen on the Toxicity of Cisplatin in LLC-PK1 Cells," *Biochemical Pharmacology* 44(2):382-387, Jul. 22, 1992.

Baldew, G.S., et al., Selective Reduction of cis-Diamminedichloroplatinum(II) Nephrotoxicity by Ebselen, *Cancer Research* 50:7031-7036, Nov. 1, 1990.

Coleman, J.K.M, et al., "Low Dose Methionine with N-Acetyl-L-Cysteine Reduces Noise-Induced Threshold Shift in the Chinchilla," ARO Abstract No. 861 25:226, Jan. 15, 2002.

Coleman, J.K.M., et al., "Post-Noise Administration of Methionine Attenuates Noise-Induced Hearing Loss in the Chinchilla," ARO Abstract No. 862 25:226, Jan. 15, 2002.

Curti, B.D., "Physical Barriers to Drug Delivery in Tumors," *Critical Reviews in Oncology/Hematology* 14:29-39, 1993.

Doi, K, et al., "Radical Scavenger Edaravone Developed for Clinical Use Ameliorates Ischemia/Reperfusion Injury in Rat Kidney," *Kidney International* 65: 1714-1723, 2004.

Duon, M., et al. "Antioxidant N-L-Acetylensteine (NAC) Can Protect Cochlea From Impulse Noise Trauma," ARO Abstract No. 860 25:226, Jan. 15, 2002.

Ekborn, A., et al., "Intracochlear Administration of Thiourea Protect Against Cisplatin Induced Ototoxicity in the Guinea Pig," ARO Abstract No. 854 25:224, Jan. 15, 2002.

Fischer, H., et al., "A Novel Biologically Active Selenoorganic Compound. VIII. Biotransformation of Ebselen," *Xenobiotica* 18(12):1347-1359, Dec. 1988.

Gillette Cloven, N., et al., "Evaluation of D-Methionine as a Cytoprotectant in Cisplatin Treatment of an Animal Model for Ovarian Cancer," *Anticancer Research* 20:4205-4209, Nov.-Dec. 2000.

Greenberg, B., et al., "Neoadjuvant Therapy for Advanced Head and Neck Cancer With Allopurinol-Modulated High Dose 5-Flourouracil and Cisplatin," *Cancer* 59(11):1860-1865, Jun. 1, 1987.

Husain, K, et al., "Carboplatin-Induced Oxidative Stress in Rat Cochlea," *Hearing Research* 158:14-22, 2001.

Iwasaka, K., et al., "Role of Hydrogen Peroxide in Cytotoxicity Induction by Ascorbates and Other Redox Compounds," *Anticancer Research* 18:4333-4337, 1998.

Jain, R.K., "Barriers to Drug Delivery in Solid Tumors," *Scientific American* 271(1):58-65, Jul. 1994.

Johnson, J.I., et al., "Relationships Between Drug Activity in NCI Preclinical In Vitro and In Vivo Models and Early Clinical Trials," *British Journal of Cancer* 84(10):1424-1431, 2001.

Kalinec, G.M., et al., "Protective Role of L-Carnitine on the Ototoxic Effects of Cisplatin in Newborn Guinea Pigs," ARO Abstract No. 855 25:225, Jan. 15, 2002.

Kern, D.H., "Heterogeneity of Drug Resistance in Human Breast and Ovarian Cancers," *Cancer Journal From Scientific American* 4(1):41-45, 1998.

Kopke, R.D., et al., "Use of Organotypic Cultures of Corti's Organ to Study the Protective Effects of Antioxidant Molecules on Cisplatin-Induced Damage of Auditory Hair Cells," *Amer. Journal of Otology* 18:559-571, 1997.

Lautermann, J., et al., "Glutathione-Dependent Antioxidant Systems in the Mammalian Inner Ear: Effects of Aging, Ototoxic Drugs and Noise," *Hearing Research* 114:75-82, 1997.

Lynch, E.D., et al., "Combined Oral Delivery of Ebselen and Allopurinol Reduces Multiple Cisplatin Toxicities in Rat Breast and Ovarian Cancer Models While Enhancing Anti-Tumor Activity," *Anti Cancer Drugs* 16(5):569-579, 2005.

Lynch, E.D., et al., "Reduction of Acute Cisplatin Ototoxicity and Nephrotoxicity in Rats by Oral Administration of Allopurinol and Ebselen," *Hearing Research* 201(1-2):81-89, Mar. 2005.

Masumoto, H., et al., "Kinetic Study of the Reaction of Ebselen With Peroxynitrite," *FEBS* 398:179-182, 1996.

Minami, T et al., "Free Radical Scavengers Suppress the Accumulation of Platinum in the Cerebral Cortex," *Biological Trace Element Research* 55(1-2):1-7, Oct.-Nov. 1996.

Muldoon, L.L., et al., "Rescue From Enhanced Alkylator-Induced Cell Death With Low Molecular Weight Sulfur-Containing Chemoprotectants," *Journal of Pharmacology and Experimental Therapeutics* 296(3):797-805, 2001.

Nakamura, Y., et al., "Ebselen, a Glutathione Peroxidase Mimetic Seleno-organic Compound, As a Multifunctional Antioxidant," *The Journal of Biological Chemistry* 277(4):2687-2694, Jan. 25, 2002.

Neuwelt, E.A., et al., "Therapeutic Efficacy of Aortic Administration of N-Acetylcysteine as a Chemoprotectant Against Bone Marrow Toxicity After Intracarotid Administration of Alkylators, With or Without Glutathione Depletion in a Rat Model," *Cancer Research* 61:7868-7874, Nov. 1, 2001.

Ogawa, A., et al., "Ebselen in Acute Middle Cerebral Artery Occlusion: A Placebo-Controlled, Double-Blind Clinical Trial," *Cerebrovascular Diseases* 9(2):112-118, Mar.-Apr. 1999.

Pourbakht, A., et al., "Ebselen has a Protective Effect on Noise Induced Hearing Loss," ARO Abstract No. 858 25:225, Jan. 15, 2002.

Ravi, R., et al., "Mechanism of Cisplatin Ototoxicity: Antioxidant System," *Pharmacology & Toxicology* 76(6):386-394, Jun. 1995.

Rose, G.S., et al., "Development and Characterization of a Clinically Useful Animal Model of Epithelial Ovarian Cancer in the Fischer 344 Rat," *American Journal of Obstetrics and Gynecology* 175(3):593-599, Sep. 1996.

Rybak, L.P., et al., "Application of Antioxidants and Other Agents to Prevent Cisplatin Ototoxicity," *Laryngoscope* 109:1740-1744, Nov. 1999.

Sakagami, H., et al., "Induction of Non-Apoptotic Cell Death by Sodium 5,6-Benzylidene-L-Ascorbate in a Human Salivary Gland Tumor Cell Line," *Anticancer Research* 19:4045-4048, 1999.

Sawa, T., et al., "Tyrosine Nitration by Peroxynitrite Formed from Nitric Oxide and Superoxide Generated by Xanthine Oxidase," The Journal of Biological Chemistry 275(42):32467-32474, Oct. 20, 2000.

Scarpidis, U., et al., "Inhibition of the JNK/c-Jun Pathway Arrests Oxidative Stress Induced Apoptosis of Rat Auditory Neurons In Vitro," ARO Abstract No. 853 25:224, Jan. 15, 2002.

Sloan Stakleff, K.D., et al., "A Novel Early-Stage Orthotopic Model for Ovarian Cancer in the Fischer 344 Rat," International Journal of Gynecological Cancer 15(2):246-254, 2005.

Smith, J.A., et al., "An Evaluation of Cytotoxicity of the Taxane and Platinum Agents Combination Treatment in a Panel of Human Ovarian Carcinoma Cell Lines," Gynecologic Oncology 98:141-145, Apr. 2, 2005.

Sogut, S., et al., "In Vivo Evidence Suggesting a Role for Purine-Catabolizing Enzymes in the Pathogenesis of Cisplatin-Induced Nephrotoxicity in Rats and Effect of Erdosteine Against This Toxicity," Cell Biochemistry and Function 22(3):157-162, May-Jun. 2004.

Tsavaris, N.B., et al., "Decreased Oral Toxicity With the Local Use of Allopurinol in Patients Who Received High Dose 5-Fluorouracil," Selective Cancer Therapeutics 7(3):113-117, 1991.

Yamaguchi, T., et al., "Ebselen in Acute Ischemic Stroke: A Placebo-Controlled, Double-Blind Clinical Trial," Stroke 29:12-17, 1998.

Yoshida, M., et al., "Prevention of Nephrotoxicity of Cisplatin by Repeated Oral Administration of Ebselen in Rats," Tohuku J. Exp. Med. Abstract 191(4):209-220, 2000.

Feghali, J.G., et al., "L-N-Acetyl-Cysteine Protection Against Cisplatin-Induced Auditory Neuronal and Hair Cell Toxicity," Laryngoscope 111(7):1147-1155, Jul. 2001.

Seidman, M.D., et al., "The Protective Effects of Allopurinol and Superoxide Dismutase on Noise-Induced Cochlear Damage," Otolaryngology—Head and Neck Surgery 109(6):1052-1056, Dec. 1993.

Suzuki, M., and M. Tsuchiya, "Ischemic Reperfusion Injury and Its Mechanism in Small Intestine," Journal of Clinical and Experimental Medicine (Igaku no Ayumi) 159(7):432, 1991. (English translation).

Zhou, Z.-B., et al., "Synthesis and Anti-Tumor Activity of Ebselen and Its Derivatives," Chemical Journal of Chinese Universities 14(2):220-222, 1993.

Database WPI, Week 200468, Thomson Scientific, London, GB; AN 2004-699386 and WO 2004/080486 A, Sep. 23, 2004.

Supplementary European Search Report dated Nov. 25, 2009, issued in corresponding European Application No. 06737379.5, filed Mar. 8, 2006.

* cited by examiner

METHODS FOR TREATING HEARING LOSS

CROSS-REFERENCE TO RELATED APPLICATION

This application is a continuation of application Ser. No. 10/337,251, filed Jan. 3, 2003, now U.S. Pat. No. 6,815,434 which claims the benefit of U.S. Provisional Application No. 60/345,813, filed Jan. 4, 2002.

FIELD OF THE INVENTION

The present invention relates to methods and compositions for treating and preventing hearing loss.

BACKGROUND OF THE INVENTION

A major cause of acquired hearing loss is loud noise. Exposure to harmful noise levels is common in the workplace. The National Institute for Occupational Safety and Health estimates that about 30 million workers in the United States encounter hazardous levels of noise. (Franks et al. (1996) *Preventing Occupational Hearing Loss—A Practical Guide*, DHHA (NIOSH) Publication No. 96-110, p. 1). These levels are encountered in, for example, construction, mining, agriculture, manufacturing and utilities, transportation, and in the military. The incidence of noise associated hearing loss continues to increase in spite of efforts to regulate job related noise exposure, and to improve the use of hearing protective devices such as ear muffs and ear plugs.

Another cause of hearing loss is exposure to ototoxic drugs such as cisplatin and aminoglycoside antibiotics. Accordingly, there is a need for methods and compositions to prevent or treat hearing loss.

SUMMARY OF THE INVENTION

In one aspect the present invention provides methods for ameliorating hearing loss, the methods each comprising the step of administering to a subject an amount of an otoprotectant composition that is effective to ameliorate hearing loss. The otoprotective composition includes at least one of the otoprotectants disclosed herein. In some embodiments, the otoprotective composition comprises a pharmaceutically effective amount of at least one glutathione peroxidase mimic (e.g., a composition comprising ebselen). In some embodiments, the otoprotective composition comprises a pharmaceutically effective amount of (a) at least one glutathione peroxidase mimic and (b) at least one xanthine oxidase inhibitor (e.g., a composition comprising ebselen and allopurinol). In some embodiments, the otoprotective composition comprises a pharmaceutically effective amount of (a) at least one glutathione peroxidase mimic and (b) at least one glutathione or glutathione precursor (e.g., a composition comprising ebselen and N-acetyl-cysteine). In some embodiments, the otoprotective composition comprises a pharmaceutically effective amount of (a) at least one xanthine oxidase inhibitor and (b) at least one glutathione or glutathione precursor (e.g., a composition comprising allopurinol and N-acetyl-cysteine). In some embodiments, the otoprotective composition comprises a pharmaceutically effective amount of (a) at least one glutathione peroxidase mimic, (b) at least one xanthine oxidase inhibitor, and (c) at least one glutathione or glutathione precursor (e.g., a composition comprising ebselen, allopurinol, and N-acetyl-cysteine).

Another aspect of the present invention provides otoprotective compositions useful for ameliorating hearing loss. The otoprotective compositions include at least one of the otoprotectants disclosed herein. In some embodiments, the otoprotective compositions comprise at least one glutathione peroxidase mimic. In some embodiments, the otoprotective compositions comprise at least one glutathione peroxidase mimic and at least one xanthine oxidase inhibitor. In some embodiments, the otoprotective compositions comprise at least one glutathione peroxidase mimic and at least one glutathione or glutathione precursor. In some embodiments, the otoprotective compositions comprise at least one xanthine oxidase inhibitor and at least one glutathione or glutathione precursor. In some embodiments, the otoprotective compositions comprise at least one glutathione peroxidase mimic, at least one xanthine oxidase inhibitor, and at least one glutathione or glutathione precursor.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
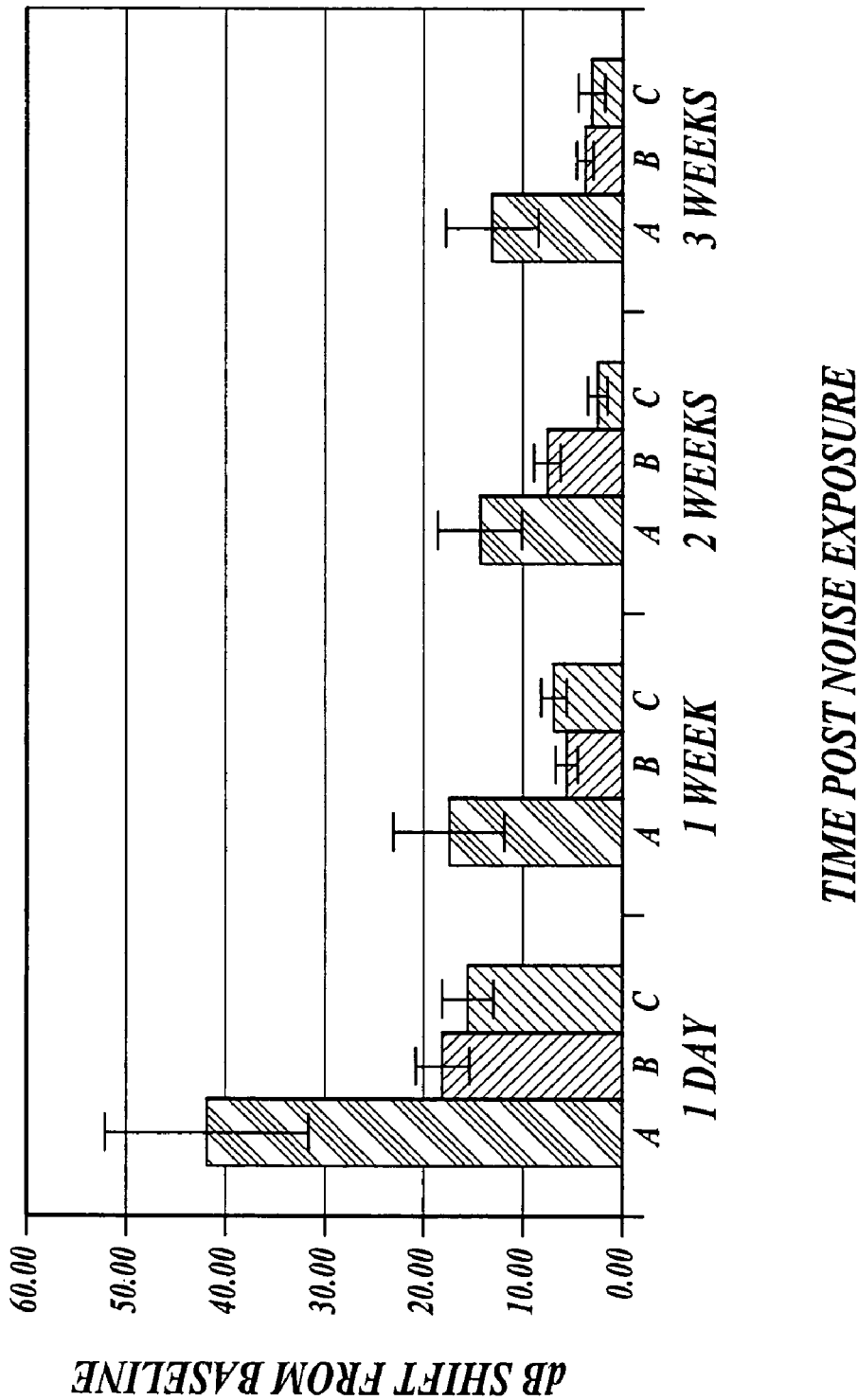
FIG. 1 shows a graph comparing the threshold shifts of the auditory evoked brainstem response (ABR) tested with a 4-16 kHz click stimulus 1 day, 1 week, 2 weeks, and 3 weeks after exposing control rats (A), N-acetyl-cysteine-treated rats (B), and ebselen-treated rats (C) to 115 dB, 4-16 kHz noise for 4 hours. The difference in threshold shifts between control and ebselen-treated rats was highly significant at 1 day, 1 week, and 2 weeks post noise exposure ($p<0.01$) and significant at 3 weeks post noise exposure ($p<0.05$). The difference in threshold shifts between control and N-acetyl-cysteine-treated rats was significant at all time points post noise exposure ($p<0.05$). Threshold shifts from baseline were measured in 5 dB intervals.

As used herein, the term "otoprotectant" refers to a chemical substance that is capable of ameliorating hearing loss.

As used herein, the term "ameliorating hearing loss" includes: (a) reducing the magnitude and/or duration of hearing loss; and/or (b) slowing the progression of hearing loss; and/or (c) preventing the onset of hearing loss that would occur without administration of an otoprotectant composition of the invention.

As used herein, the term "ototoxic agent" means an agent that is likely to impair the function of any component of the ear involved in hearing and, therefore, is likely to induce temporary or permanent hearing loss. Examples of ototoxic agents are ototoxic drugs and ototoxic noise.

As used herein, the term "exposure to an ototoxic agent" includes single or multiple exposures to an ototoxic agent that is recognized in the art as being likely to cause temporary or permanent hearing loss. For example, the Occupational Safety and Health Administration (OSHA) considers exposures to noise greater than or equal to 85 decibels (dB) to be hazardous to hearing. Thus, OSHA mandates that workers not be exposed to greater than or equal to 85 dB of noise over a continuous eight hour period based on a time weighted average, unless noise reduction measures (i.e., ear muffs) are employed.

As used herein, the term "otoprotectant composition" refers to a composition that includes at least one otoprotectant, and may include more than one otoprotectant. Otoprotectant compositions may also include, in addition to one or more otoprotectant(s), pharmaceutically acceptable carriers that facilitate administration of an otoprotectant composition to a mammalian subject.

In one aspect the present invention provides methods for ameliorating hearing loss, the methods each comprising the step of administering to a subject an amount of an otoprotectant composition that is effective to ameliorate hearing loss. The methods of the invention are applicable to any mammalian subject, such as a human subject. The otoprotectant composition may be administered before, during or after exposure to an ototoxic agent.

The otoprotectant compositions can include one or more than one otoprotectant. Unless stated otherwise, any isomeric or tautomeric form of any of the otoprotectants disclosed herein can be used in the invention. Some otoprotectants that can be included in otoprotectant compositions of the invention include glutathione and glutathione precursors. Representative examples of otoprotectants in this category are: methionine; N-acetyl-DL-methionine; S-adenosylmethionine; cysteine; homocysteine; N-acetylcysteine; glutathione; glutathione ethylester; glutathione diethylester; glutathione triethylester; cysteamine; cystathione; N,N'-diacetyl-L-cystine (DiNAC); 2(R,S)-D-ribo-(1',2',3',4'-tetrahydroxybutyl)-thiazolidine-4(R)-carboxylic acid (RibCys); 2-alkylthiazolidine 2(R,S)-D-ribo-(1',2',3',4'-tetrahydroxybutyl) thiazolidine (RibCyst); and 2-oxo-L-thiazolidine-4-carboxylic acid (OTCA).

Xanthine oxidase inhibitors, for example allopurinol ($C_5H_4N_4O$) and its tautomers, are useful as otoprotectants in the practice of the invention. The following representative allopurinol derivatives are useful as otoprotectants in the practice of the invention: 1-methylallopurinol; 2-methylallopurinol; 5-methylallopurinol; 7-methylallopurinol; 1,5-dimethylallopurinol; 2,5-dimethylallopurinol; 1,7-dimethylallopurinol; 2,7-dimethylallopurinol; 5,7-dimethylallopurinol; 2,5,7-trimethylallopurinol; 1-ethoxycarbonylallopurinol; and 1-ethoxycarbonyl-5-methylallopurinol.

Glutathione peroxidase mimics are useful as otoprotectants in the practice of the invention. Representative examples of glutathione peroxidase mimics include: 2-phenyl-1,2-benzoisoselenazol-3(2H)-one (ebselen); 6A,6B-diseleninic acid-6A',6B'-selenium bridged β-cyclodextrin (6-diSeCD); and 2,2'-diseleno-bis-Beta-cyclodextrin (2-diSeCD).

Table 1 sets forth representative effective dosage ranges for some of the otoprotectants described herein. The otoprotectants set forth in Table 1 are preferably administered orally or intravenously. The otoprotectants set forth in Table 1 can be administered to a mammalian subject before, during or after exposure to an ototoxic agent, such as ototoxic noise. Typically, a mammalian subject receives at least one dose of at least one otoprotectant before and after each exposure to an ototoxic agent. In some embodiments, a mammalian subject receives one dose of at least one otoprotectant before exposure to an ototoxic agent and at least one dose of at least one otoprotectant after exposure to an ototoxic agent. In some embodiments, a mammalian subject receives at least two daily doses of at least one otoprotectant for a single exposure to an ototoxic agent, such as an exposure to ototoxic noise lasting for about 1 to about 6 hours. In some embodiments, a mammalian subject receives at least three daily doses of at least one otoprotectant for repeated exposures to an ototoxic agent or prolonged exposures to an ototoxic agent, such as exposures to ototoxic noise lasting longer than about 6 hours.

In some embodiments of the invention, an otoprotectant composition comprising one or more otoprotectants is administered to a mammalian subject at one or more times during a period extending from 18 hours before exposure of the mammalian subject to an ototoxic agent, to 18 hours after exposure of the mammalian subject to an ototoxic agent. In some embodiments of the invention, an otoprotectant composition comprising one or more otoprotectants is administered to a mammalian subject at one or more times during a period extending from one hour before exposure of the mammalian subject to an ototoxic agent, to one hour after exposure of the mammalian subject to an ototoxic agent. In some embodiments of the invention, an otoprotectant composition comprising one or more otoprotectants is administered to a mammalian subject at one or more times during a period extending from 30 minutes before exposure of the mammalian subject to an ototoxic agent, to 30 minutes after exposure of the mammalian subject to an ototoxic agent. In some embodiments of the invention, an otoprotectant composition comprising one or more otoprotectants is administered to a mammalian subject at one or more times during a period extending from 10 minutes before exposure of the mammalian subject to an ototoxic agent, to ten minutes after exposure of the mammalian subject to an ototoxic agent. In some embodiments of the invention, an otoprotectant composition comprising one or more otoprotectants is administered to a mammalian subject concurrently with exposure of the mammalian subject to an ototoxic agent, such as ototoxic noise.

The abbreviation "mg" means milligrams.

TABLE 1

Dosage Ranges for Otoprotectants

| Compound(s) | Chemical name | Presently preferred range | Presently more preferred range | Presently most preferred range |
|---|---|---|---|---|
| NAM | N-acetyl-Methionine | 5-5000 mg/day | 50-2000 mg/day | 500-1000 mg/day |
| Methionine | Methionine | 5-5000 mg/day | 50-2000 mg/day | 500-1000 mg/day |
| SAM | S-adenosyl-Methionine | 5-5000 mg/day | 50-2000 mg/day | 500-1000 mg/day |
| Cysteine | Cysteine | 5-5000 mg/day | 50-2000 mg/day | 500-1000 mg/day |
| NAC | N-acetyl-L-Cysteine | 5-5000 mg/day | 50-2000 mg/day | 500-1000 mg/day |
| DiNAC | N,N'-diacetyl-cystine | 5-5000 mg/day | 50-2000 mg/day | 500-1000 mg/day |
| homocysteine | homocysteine | 5-5000 mg/day | 50-2000 mg/day | 500-1000 mg/day |
| RibCyst | 2-alkylthiazolidine, 2(R,S)-D-ribo-(1',2',3',4'-tetrahydroxybutyl)thiazolidine | 5-5000 mg/day | 50-2000 mg/day | 500-1000 mg/day |
| RibCys | 2(R,S)-D-ribo-(1',2'3',4'-tetrahydroxybutyl)-thiazolidine-4(R)-carboxylic acid | 5-5000 mg/day | 50-2000 mg/day | 500-1000 mg/day |
| Cystathione | Cystathione | 5-5000 mg/day | 50-2000 mg/day | 500-1000 mg/day |
| Glutathione | Glutathione | 5-5000 mg/day | 50-2000 mg/day | 500-1000 mg/day |
| Glutathione ethyl ester | Glutathione ethyl ester | 5-5000 mg/day | 50-2000 mg/day | 500-1000 mg/day |
| Glutathione diethyl ester | Glutathione diethyl ester | 5-5000 mg/day | 50-2000 mg/day | 500-1000 mg/day |
| Glutathione triethyl ester | S-(1,2-dicarboxyethyl)glutathione triester | 5-5000 mg/day | 50-2000 mg/day | 500-1000 mg/day |
| Cysteamine | Cysteamine | 5-5000 mg/day | 50-2000 mg/day | 500-1000 mg/day |
| OTCA | 2-oxo-L-thiazolidine-4-carboxylic acid | 5-5000 mg/day | 50-2000 mg/day | 500-1000 mg/day |
| Ebselen | 2-phenyl-1,2-benzoisoselenazol-3(2H)-one | 5-5000 mg/day | 50-2000 mg/day | 500-1000 mg/day |
| 2-diSeCD | 2,2'-diseleno-bis-Beta-cyclodextrin | 5-5000 mg/day | 50-2000 mg/day | 500-1000 mg/day |
| 6-diSeCD | 6A,6B-diseleninic acid-6A',6B'-selenium bridged beta-cyclodextrin | 5-5000 mg/day | 50-2000 mg/day | 500-1000 mg/day |
| Allopurinol | 4-hydroxypyrazolo[3,4-d]pyrimidine | 10-2400 mg/day | 50-1200 mg/day | 100-800 mg/day |
| 1-methylallopurinol | | 10-2400 mg/day | 50-1200 mg/day | 100-800 mg/day |
| 2-methylallopurinol | | 10-2400 mg/day | 50-1200 mg/day | 100-800 mg/day |
| 5-methylallopurinol | | 10-2400 mg/day | 50-1200 mg/day | 100-800 mg/day |
| 7-methylallopurinol | | 10-2400 mg/day | 50-1200 mg/day | 100-800 mg/day |
| 1,5-dimethylallopurinol | | 10-2400 mg/day | 50-1200 mg/day | 100-800 mg/day |
| 2,5-dimethylallopurinol | | 10-2400 mg/day | 50-1200 mg/day | 100-800 mg/day |
| 1,7-dimethylallopurinol | | 10-2400 mg/day | 50-1200 mg/day | 100-800 mg/day |
| 2,7-dimethylallopurinol | | 10-2400 mg/day | 50-1200 mg/day | 100-800 mg/day |
| 5,7-dimethylallopurinol | | 10-2400 mg/day | 50-1200 mg/day | 100-800 mg/day |
| 1-ethoxycarbonylallopurionol | | 10-2400 mg/day | 50-1200 mg/day | 100-800 mg/day |
| 1-ethoxycarbonyl-5-methylallopurinol | | 10-2400 mg/day | 50-1200 mg/day | 100-800 mg/day |

The otoprotectant compositions can include one, or more than one, otoprotectant(s). Thus, otoprotectant compositions of the invention can include any combination of any of the individual otoprotectants described herein. In some embodiments of the otoprotectant compositions that include more than one otoprotectant, the otoprotectant compositions are formulated to provide an effective dosage of the individual constituent otoprotectants as set forth in Table 1. In some embodiments, the combination of otoprotectants may act synergistically, as described in EXAMPLE 2.

In another aspect, the present invention provides otoprotectant compositions that each comprise at least two (e.g., two, three, four, five, six, seven, eight, nine, or ten) of the individual otoprotectants disclosed herein. For example, some otoprotectant compositions include at least one otoprotectant selected from Group A, at least one otoprotectant selected from Group B, and at least one otoprotectant selected from Group C, wherein Groups A, B and C include the following otoprotectants:

Group A (glutathione or a glutathione precursor): methionine; N-acetyl-DL-methonine methionine; S-adenosylmethionine; cysteine; N-acetylcysteine; glutathione; glutathione ethylester; glutathione diethylester; glutathione triethylester; DiNAC; RibCys; homocysteine; cystathione; cysteamine; OTCA and RibCyst.

Group B (xanthine oxidase inhibitors): allopurinol; 1-methylallopurinol; 2-methylallopurinol; 5-methylallopurinol; 7-methylallopurinol; 1,5-dimethylallopurinol; 2,5-dimethylallopurinol; 1,7-dimethylallopurinol; 2,7-dimethylallopurinol; 5,7-dimethylallopurinol 2,5,7-trimethylallopurinol; 1-ethoxycarbonylallopurinol; and 1-ethoxycarbonyl-5-methylallopurinol.

Group C (glutathione peroxidase mimics): Ebselen; 2-diSeCD; and 6-diSeCD.

The otoprotectant compositions of the invention are useful, for example, for ameliorating hearing loss induced by exposure to an ototoxic agent. The otoprotectant compositions of the invention can be used in the methods of the invention for ameliorating hearing loss induced by an ototoxic agent, for example, hearing loss induced by exposure to ototoxic noise.

The otoprotectant compositions of the invention can be formulated to provide a dosage that is effective to ameliorate hearing loss in a subject exposed to an ototoxic agent. For example, in some embodiments the otoprotectant compositions are formulated to provide an effective dosage of the individual otoprotectants as set forth in Table 1.

Administration of the otoprotectant compositions of the invention is accomplished by any effective route, e.g., orally or parenterally, as described in EXAMPLES 1-3. Methods of parenteral delivery include topical, intra-arterial, subcutaneous, intramedullary, intravenous, or intranasal administration. In addition to one or more otoprotectants, the otoprotectant compositions may contain suitable pharmaceutically acceptable carriers comprising excipients and other compounds that facilitate administration of the otoprotectant compositions to a mammalian subject. Further details on techniques for formulation and administration may be found in the latest edition of "Remington's Pharmaceutical Sciences" (Maack Publishing Co, Easton, Pa.).

Otoprotectant compositions for oral administration can be formulated using pharmaceutically acceptable carriers well known in the art, in dosages suitable for oral administration, as described in EXAMPLES 1-3. Such carriers enable the otoprotectant compositions to be formulated as tablets, pills, dragees, capsules, liquids, gels, syrups, slurries, suspensions, etc., suitable for ingestion by a subject.

Otoprotectant compositions for oral use can be obtained, for example, through combination of one or more otoprotectants with solid excipient, optionally grinding the resulting mixture, and processing the mixture of granules, after adding suitable additional compounds, if desired, to obtain tablets or dragee cores. Suitable excipients include carbohydrate or protein fillers. These include, but are not limited to, sugars, including lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins, such as gelatin and collagen. If desired, disintegrating or solubilising agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterise the quantity of active compound (i.e., dosage).

Otoprotectant compositions, which can be used orally, can be formulated, for example, as push-fit capsules made of gelatin, as well as soft, sealed capsules made of gelatin and a coating such as glycerol or sorbitol. Push-fit capsules can contain otoprotectants mixed with filler or binders such as lactose or starches, lubricants such as talc or magnesium stearate, and, optionally, stabilizers. In soft capsules, the otoprotectant(s) may be dissolved or suspended in suitable liquids, such as fatty oils, liquid paraffin, or liquid polyethylene glycol with or without stabilizers.

Otoprotectant compositions for parenteral administration include aqueous solutions of one or more otoprotectants, as described in EXAMPLES 1-3. For injection, the otoprotectant compositions of the invention may be formulated in aqueous solutions, preferably in physiologically compatible buffers such as Hank's solution, Ringer's solution, or physiologically buffered saline. Aqueous injection suspensions may contain substances, which increase the viscosity of the suspension, such as sodium carboxymethyl cellulose, sorbitol, or dextran. Additionally, suspensions of otoprotectants may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents, which increase the solubility of the compounds to allow for the preparation of highly concentrated solutions.

For topical or nasal administration, penetrants appropriate to the particular barrier to be permeated are typically used in the formulation. Such penetrants are generally known in the art.

The otoprotectant compositions of the present invention may be manufactured in a manner similar to that known in the art (e.g., by means of conventional mixing, dissolving, granulating, dragee-making, levigating, emulsifying, encapsulating, entrapping or lyophilising processes). The otoprotectant compositions may also be modified to provide appropriate release characteristics, e.g., sustained release or targeted release, by conventional means (e.g., coating).

The otoprotectant compositions may be provided as a salt and can be formed with many acids, including but not limited to hydrochloric, sulfuric, acetic, lactic, tartaric, malic, succinic, etc. Salts tend to be more soluble in aqueous or other protonic solvents than are the corresponding free base forms.

After such otoprotectant compositions formulated in an acceptable carrier have been prepared, they can be placed in an appropriate container and labeled for use.

The amount actually administered will be dependent upon the individual to which treatment is to be applied, and will preferably be an optimized amount such that the desired effect is achieved without significant side-effects. The determination of an effective dose is well within the capability of those skilled in the art. Of course, the skilled person will realize that divided and partial doses are also within the scope of the invention.

For any otoprotectant composition, the effective dose can be estimated initially either in cell culture assays or in any appropriate animal model (e.g., primate, rats and guinea pigs and other small laboratory animals), as described in EXAMPLES 1-3. The animal model is also typically used to achieve a desirable concentration range and route of administration. Such information can then be used to determine useful doses and routes for administration in humans or other mammals.

Therapeutic efficacy and possible toxicity of otoprotectant compositions can be determined by standard pharmaceutical procedures, in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio $ED_{50}/LD_{50}$. Otoprotectant compositions which exhibit large therapeutic indices are preferred. The data obtained from cell culture assays and animal studies is used in formulating a range of dosage for use in humans or other mammals. The dosage of such compounds lies preferably within a range of circulating concentrations that include the $ED_{50}$ with little or no toxicity. The dosage typically varies within this range depending upon the dosage form employed, sensitivity of the patient, and the route of administration.

Example 1

This example shows that ebselen administration protects against hearing threshold shifts and cochlear hair cell loss in rats exposed to noise.

1. Methods

Noise exposure paradigm: 8-week old female Fisher-344 rats were exposed to 110-115 dB noise at 4-16 kHz for 4 hours.

Physiologic analyses: The auditory evoked brainstem response (ABR) was used to assess hearing in each ear in each animal before and after exposure to noise using equipment from Intelligent Hearings System. ABR generated with a click stimulus (broad spectrum stimulus, 4-16 kHz) was measured in 5 dB intervals. Animals were re-evaluated evaluated at 1 day, 1 week, 2 weeks, and 3 weeks post noise exposure. ABR changes measured 1 day post noise exposure are considered to represent a temporary threshold shift (TTS); ABR changes measured 3 weeks post noise exposure are considered to represent a permanent threshold shift (PTS).

Morphologic analyses: Hair cell counts in cochlea from test animals following noise exposure and physiologic evaluation using ABR were determined by carefully dissecting cochlea to obtain inner ear sensory epithelia. The tissues were stained with fluorescein-labeled phalloidin (specific for actin filaments, which are abundant in hair cells) and 4,6-diamidino-2-phenylindole (DAPI; specific for the DNA in the nucleus in cells). Samples were then mounted on microscope slides and viewed with epifluorescence to determine the extent of hair cell loss and retention. The correlation between physiologic data (ABR) and morphological data (hair cell counts) allows for confirmation of the protective effects of otoprotectants of the invention.

Dosing of Otoprotectants: Ebselen was dissolved at 4 mg/mL in 10% DMSO and administered to rats at 16 mg/kg. N-acetyl-cysteine was dissolved at 100 mg/mL in saline and was administered to rats at 325 mg/kg. About 0.5 ml of ebselen solution or N-acetyl-cysteine solution was injected intra-peritoneally or delivered by oral gavage twice daily the day prior to, the day of, and the day following exposure to noise. Control animals were dosed on an identical schedule with vehicle (10% DMSO) only.

Statistical analysis: All experiments were performed with four rats per study group, and measuring each ear independently before and after noise exposure. Data was collected in blinded studies. Statistical analyses were performed by analysis of variance (ANOVA) between study groups.

2. Results

As shown in FIG. 1, ABR data generated with a 4-16 kHz click stimulus measured in 5 dB intervals show a highly significant reduction in TTS in animals administered ebselen at one day after noise exposure, and a significant reduction in PTS at three weeks after noise exposure, compared with controls. The reduction in TTS and PTS in animals administered ebselen was at least two-fold, compared to control animals. Similarly, the ABR data show a significant reduction in TTS in animals administered N-acetyl-cysteine acetyl-cysteine at all time points after noise exposure.

The physiologic data correlates with morphologic data from the same test animals showing less hair cell loss in cochlea from animals treated with otoprotectants compared to the control group. For example, in an ebselen-treated animal with 0 dB PTS and a significantly reduced TTS, preservation of most outer hair cells was observed, whereas there was almost complete loss of outer hair cells in a control animal with a 15 dB PTS. Similar preservation of outer hair cells was observed in N-acetyl-cysteine-treated rats. Therefore, the administration of ebselen or N-acetyl-cysteine results in physiologic protection from noise-induced hearing loss and hair cell loss.

Similarly, the administration of allopurinol was found to provide protection from noise-induced hearing loss and hair cell loss (see EXAMPLE 2).

Example 2

This example shows that combined administration of ebselen and allopurinol provides greater protection from hearing loss than each compound administered alone.

1. Methods

Noise exposure paradigm: 8-10 week old female Fisher-344 rats were exposed to 110-115 dB noise at 4-16 kHz for 4 hours.

Physiologic analyses: ABR generated with a click stimulus (broad spectrum stimulus, 4-16 kHz), and with tone stimuli at frequencies of 4 kHz, 8 kHz, 12 kHz, and 16 kHz, was measured in 5 dB intervals, as described in EXAMPLE 1. Animals were tested before and at 3 weeks post noise exposure to assess PTS.

Dosing of compounds: Ebselen was dissolved at 4 mg/ml in 10% DMSO and allopurinol was dissolved at 4 mg/ml in water. Ebselen and allopurinol were administered to rats at an individual dose of 16 mg/kg or at a combined dose of 8 mg/kg each. About 0.5 ml of ebselen solution, allopurinol solution, or ebselen/allopurinol solution was injected intra-peritoneally or delivered by oral gavage twice daily the day prior to, the day of, and the day following exposure to noise. Control animals were dosed on an identical schedule with vehicle only.

Statistical analysis: All experiments were performed with four rats per study group, and measuring each ear independently before and after noise exposure. Data was collected in blinded studies. Statistical analyses were performed by ANOVA between study groups.

2. Results

Figure 2:
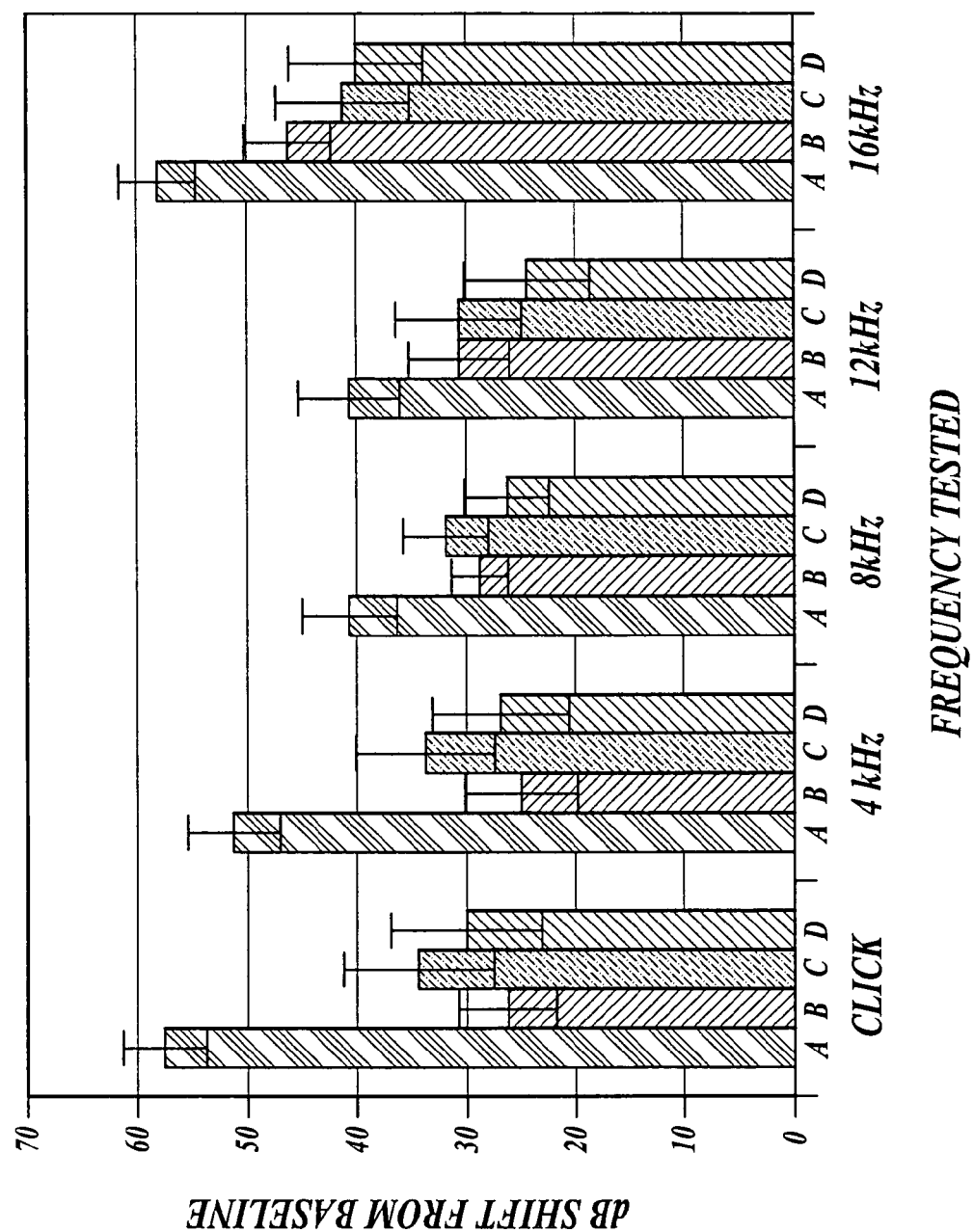
FIG. 2 shows a graph comparing the threshold shifts of the ABR tested with a 4-16 kHz click stimulus, and stimuli at frequencies of 4 kHz, 8 kHz, 12 kHz, and 16 kHz, 3 weeks after exposing control rats (A), 16 mg/kg ebselen-treated rats (B), 16 mg/kg allopurinol-treated rats (C), and 8 mg/kg ebselen/allopurinol-treated rats (D) to 115 dB, 4-16 kHz noise for 4 hours. The difference in threshold shifts between control (A) and ebselen-treated rats (B) was highly significant for the click and 4 kHz stimuli ($p<0.01$). The difference in threshold shifts between control (A) and allopurinol-treated rats (C) was highly significant for the click, 4 kHz, and 16 kHz stimuli ($p<0.01$). The difference in threshold shifts between control (A) and ebselen/allopurinol-treated rats (C) was highly significant for the click, 4 kHz, and 16 kHz stimuli ($p<0.01$) and significant for the 12 kHz stimulus ($p<0.05$). Threshold shifts from baseline were measured in 5 dB intervals.

Physiologic data as measured by ABR indicates that ebselen and allopurinol, alone or in combination, afford significant protection from both temporary and permanent thresholds shifts in rats exposed to noise. FIG. 2 shows that ebselen and allopurinol delivered by intra-peritoneal injection at 16 mg/kg individually result in significant reductions in PTS at three weeks after noise exposure, compared with controls. At half the individual dose (i.e., 8 mg/kg each), the combination of ebselen and allopurinol provides a level of protection that is greater than additive (synergy).

Example 3

This example shows that ebselen administration protects against hearing threshold shifts and cochlear hair cell loss in rats repeatedly exposed to noise.

1. Methods

Noise exposure paradigm: 8-week old female Fisher-344 rats were exposed to 110 dB noise at 4-16 kHz for 4 hours two times three weeks apart.

Physiologic analyses: ABR generated with tone stimuli at frequencies of 4 kHz, 8 kHz, 12 kHz, and 16 kHz, was measured in 5 dB intervals, as described in EXAMPLE 1. Animals were tested before and 3 weeks following the repeated noise exposure to evaluate permanent threshold shift (PTS).

Morphologic analyses: Hair cell counts in cochlea from test animals following noise exposure and physiologic evaluation using ABR were determined as described in EXAMPLE 1.

Dosing of Ebselen: Ebselen was dissolved at 4 mg/mL in 10% DMSO and administered to rats at a dose of 16 mg/kg. About 0.5 ml of ebselen solution was injected intra-peritoneally or delivered by oral gavage twice daily the day prior to, the day of, and the day following each exposure to noise. Control animals were dosed on an identical schedule with vehicle only.

Statistical analysis: All experiments were performed with four rats per study group, and measuring each ear independently before and after noise exposure. Data was collected in blinded studies. Statistical analyses were performed by ANOVA between study groups.

2. Results

Figure 3:
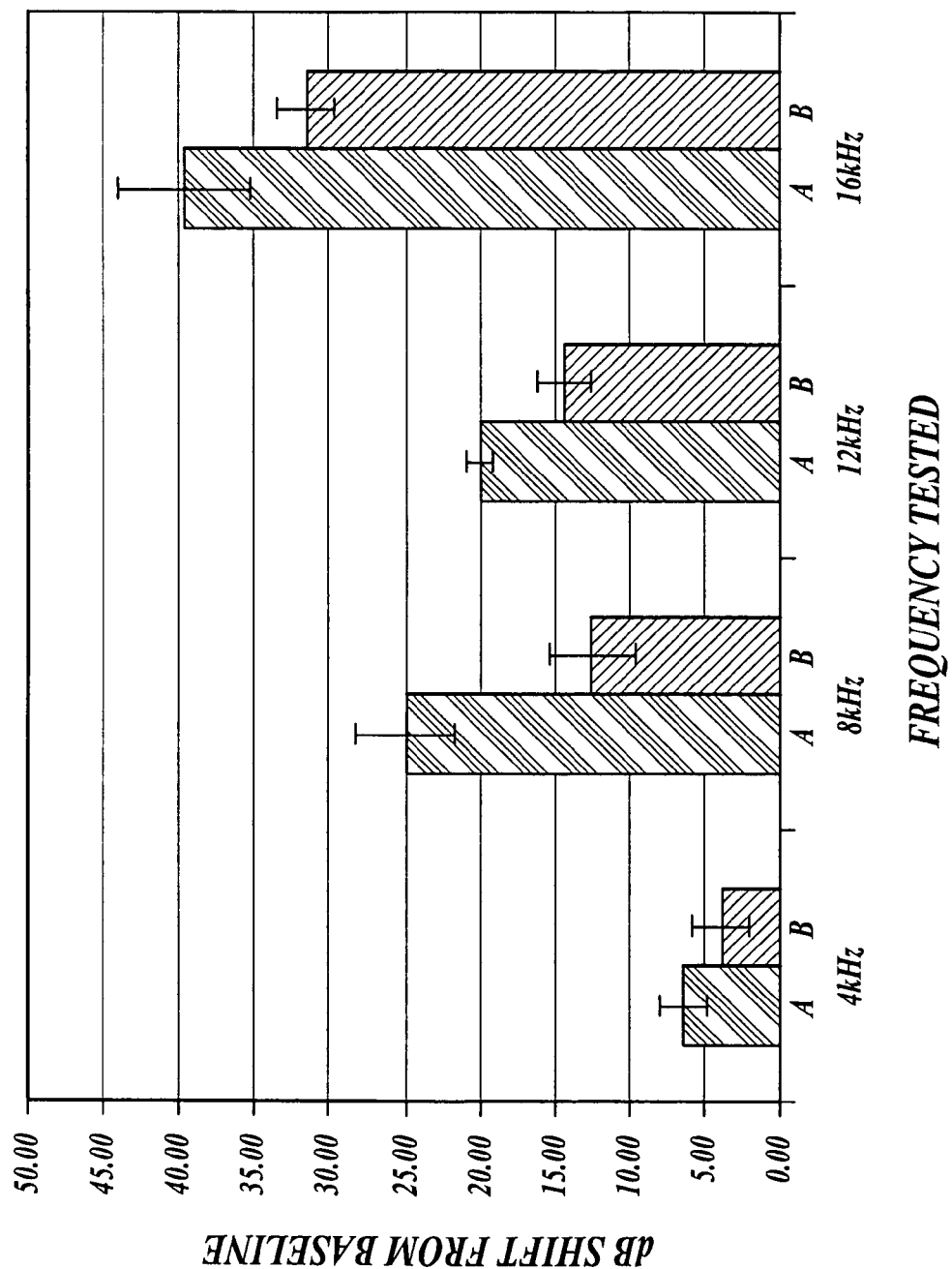
FIG. 3 shows a graph comparing the threshold shifts of the ABR tested with stimuli at frequencies of 4 kHz, 8 kHz, 12 kHz, and 16 kHz, 3 weeks after exposing control rats (A) and ebselen-treated rats (B) two times to 110 dB, 4-16 kHz noise for 4 hours, separated by three weeks. The difference in threshold shifts between control and ebselen-treated rats was highly significant for the 8 kHz stimulus ($p<0.01$), and significant for the 16 kHz stimulus ($p<0.05$). Threshold shifts from baseline were measured in 5 dB intervals.
Figure 4A:
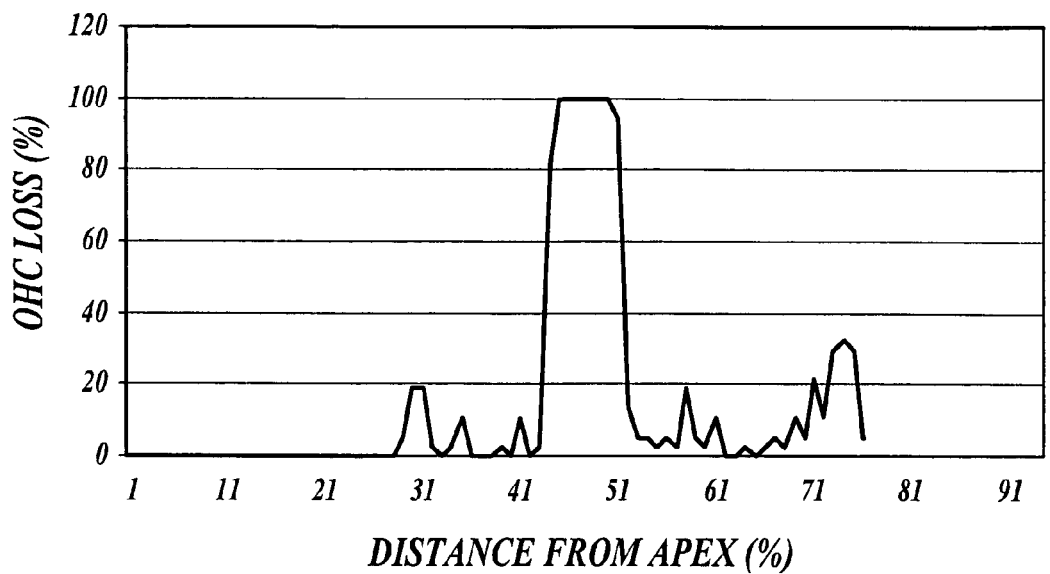
FIG. 4A-D shows graphs comparing the percentage of outer hair cell loss as a function of distance from the apex of the cochlea, after exposing control rats (A and C) and 16 mg/kg ebselen treated-rats (B and D) at two times, separated by three weeks, to 110 dB, 4-16 kHz noise for 4 hours. The number of outer hair cells lost in rats A and C was 401 and 246, respectively; the number of outer hair cells lost in rats B and D was 90 and 56, respectively.
Figure 4B:
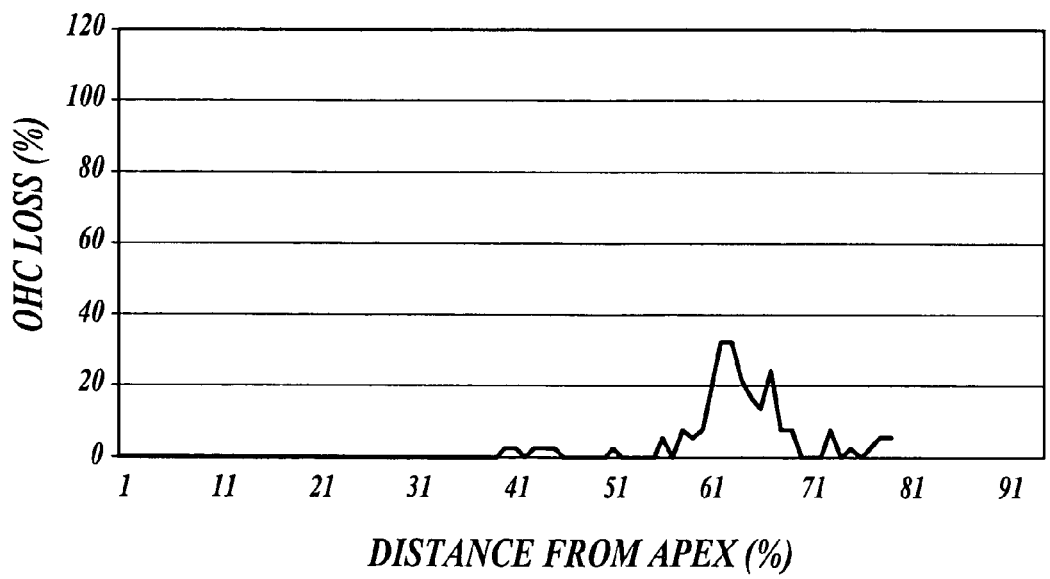
Figure 4C:
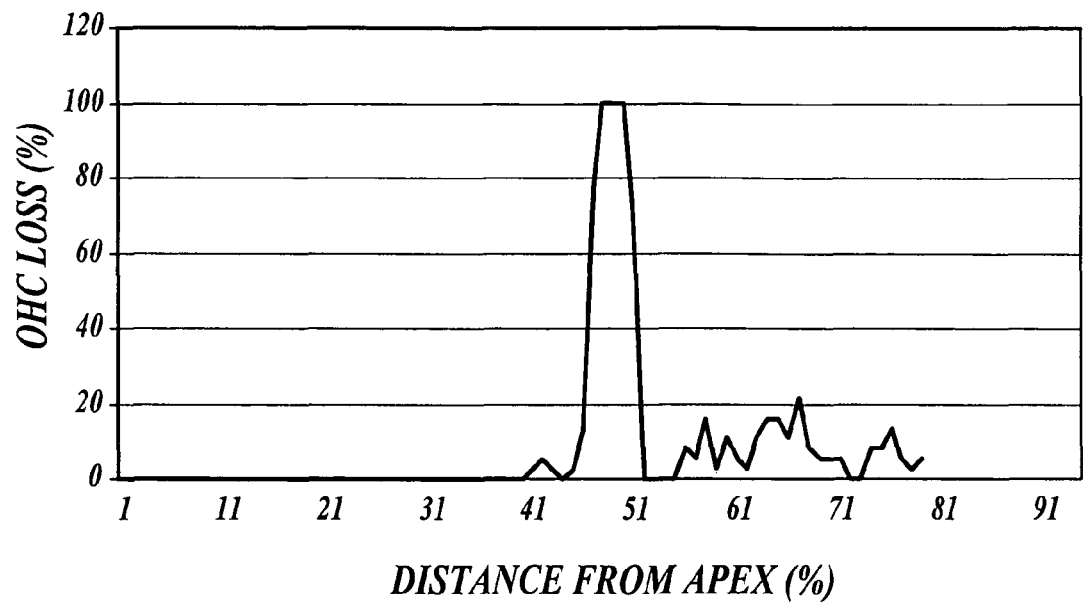
Figure 4D:
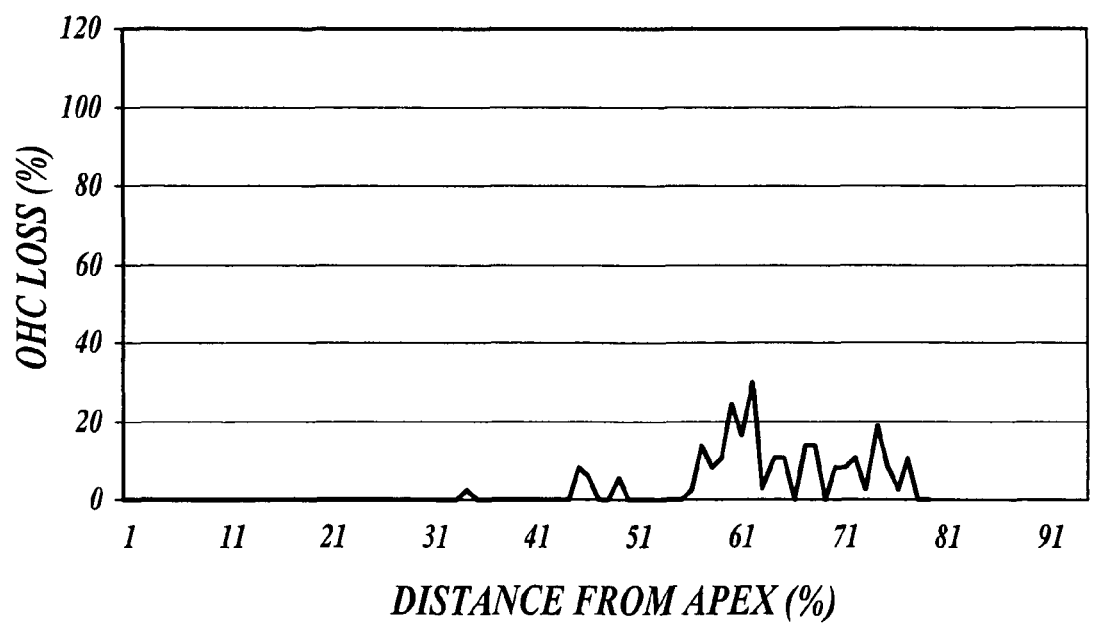

Physiologic data measured by ABR indicates that ebselen provides significant protection from both temporary and permanent threshold shifts in rats from repeated exposure to noise. The administration of ebselen results in a significant reduction in TTS at 1 day after repeated noise exposures, compared with controls. In addition, the PTS at three weeks after repeated noise exposures was significantly reduced in these animals compared to controls, as shown in FIG. 3. The physiologic data correlates with morphologic data from the same test animals showing less hair cell loss in cochlea from animals treated with ebselen compared to the control group, as shown in FIG. 4.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for ameliorating hearing loss in a mammalian subject, comprising the step of administering to a mammalian subject an amount of an otoprotective composition effective to ameliorate hearing loss, wherein the otoprotective composition comprises:

(a) a pharmaceutically effective amount of at least one otoprotectant selected from the group consisting of allopurinol, 1-methylallopurinol, 2-methylallopurinol, 5-methylallopurinol, 7-methylallopurinol, 1,5-dimethylallopurinol, 2,5-dimethylallopurinol, 1,7-dimethylallopurinol, 2,7-dimethylallopurinol, 5,7-dimethylallopurinol, 2,5,7-trimethylallopurinol, 1-ethoxycarbonylallopurinol, 1-ethoxycarbonyl-5-methylallopurinol, and pharmaceutically effective salts thereof; and (b) a pharmaceutically effective amount of at least one otoprotectant selected from the group consisting of methionine, N-acetyl-DL-methionine, S-adenosylmethionine, cysteine, homocysteine, cysteamine, N-acetylcysteine, glutathione, glutathione ethylester, glutathione diethylester, glutathione triethylester, cysteamine, cystathione, N,N'-diacetyl-L-cysteine (DiNAC), 2(R,S)-D-ribo-(1',2',3',4'-tetrahydroxybutyl)-thiazolidine-4(R)-carboxylic acid (RibCys), 2-alkylthiazolidine 2(R,S)-D-ribo-(1',2',3',4'-tetrahydroxybutyl)thiazolidine (RibCyst), 2-oxo-L-thiazolidine-4-carboxylic acid (OTCA), and pharmaceutically effective salts thereof.

2. The method of claim 1, wherein the composition comprises allopurinol and N-acetylcysteine, or pharmaceutically effective salts thereof.

3. The method of claim 1, wherein the mammalian subject is a human subject.

4. The method of claim 1, wherein each of the otoprotectants in group (a) is present in an amount of 10-2400 mg and each of the otoprotectants in group (b) is present in an amount of 5-5000 mg.

5. The method of claim 1, wherein each of the otoprotectants in group (a) is present in an amount of 50-1200 mg and each of the otoprotectants in group (b) is present in an amount of 50-2000 mg.

6. The method of claim 1, wherein each of the otoprotectants in group (a) is present in an amount of 100-800 mg and each of the otoprotectants in group (b) is present in an amount of 500-1000 mg.

* * * * *